United States Patent [19]

Han et al.

[11] Patent Number: 4,982,023
[45] Date of Patent: Jan. 1, 1991

[54] OXIDATION OF METHANE TO METHANOL

[75] Inventors: Scott Han, Lawrenceville, N.J.; Robert E. Palermo, New Hope; Dennis E. Walsh, Richboro, both of Pa.

[73] Assignee: Mobil Oil Corporation, Fairfax, Va.

[21] Appl. No.: 422,365

[22] Filed: Oct. 16, 1989

[51] Int. Cl.$^5$ .................. C07C 29/50; C07C 31/04
[52] U.S. Cl. .................. 568/910.5; 568/910
[58] Field of Search .................. 568/910.5, 910

[56] References Cited

U.S. PATENT DOCUMENTS

| | | | |
|---|---|---|---|
| 1,976,790 | 10/1934 | Lewis et al. | 568/910.5 |
| 2,004,714 | 6/1935 | Thompson et al. | 548/910.5 |
| 2,186,688 | 1/1940 | Walker | 568/910.5 |
| 4,243,613 | 1/1981 | Brockhaus et al. | 568/910 |
| 4,618,732 | 10/1986 | Gesser et al. | 568/910 |
| 4,760,210 | 7/1988 | Sweeney | 568/910 |

Primary Examiner—J. E. Evans
Attorney, Agent, or Firm—Alexander J. McKillop; Charles J. Speciale; Edward F. Kenehan, Jr.

[57] ABSTRACT

A marked improvement in yield, in selectivity or in both is obtained in the synthesis of methanol by the homogeneous direct partial oxidation of natural gas or other source of methane when the reactor space is filled with inert, refractory inorganic particles.

11 Claims, 1 Drawing Sheet

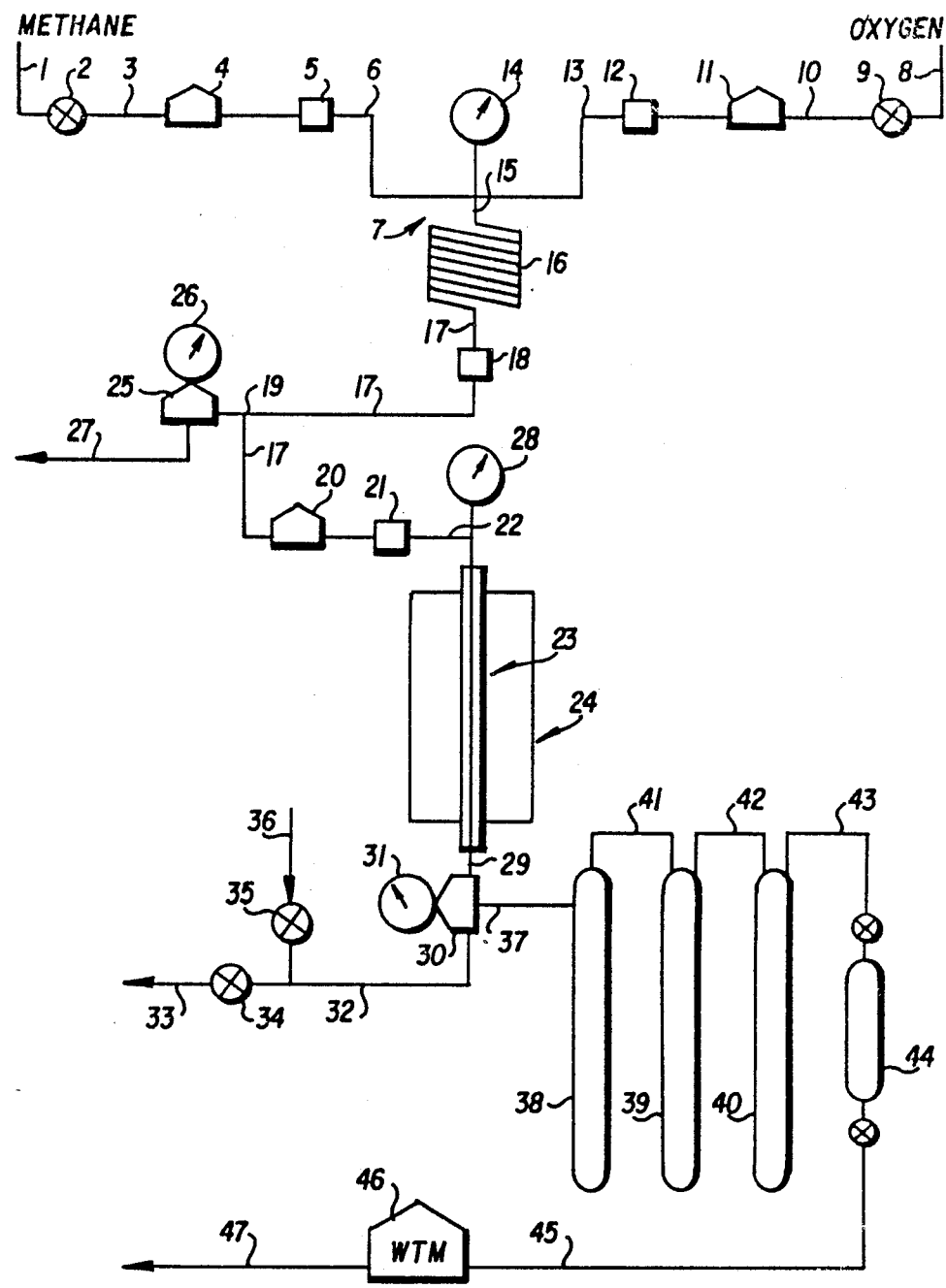

OXIDATION OF METHANE TO METHANOL

FIELD OF THE INVENTION

This invention pertains to the direct partial oxidation of a gaseous feed comprising a source of methane to normally liquid products. More particularly, it pertains to converting a gaseous feed comprising natural gas admixed with gaseous oxygen to methanol and other liquid oxygenated organic products.

BACKGROUND OF THE INVENTION

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85–95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses, no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficultly accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a very limited market and does not appear to offer a practical way to utilize natural gas from remote fields. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for better ways to convert natural gas to higher valued and/or more readily transportable products.

A reaction which has been extensively studied for many years is the direct partial oxidation of methane to methanol. This route, involving essentially the reaction of methane and gaseous oxygen according to the simple equation

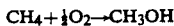

$$CH_4 + \tfrac{1}{2}O_2 \rightarrow CH_3OH$$

could theoretically produce methanol with no by-product. The homogeneous reaction of methane with oxygen occurs most favorably under high pressure (10 to 200 atm.), moderate temperatures, (350°–500° C.), and at relatively low oxygen concentration. Oxidation to formaldehyde and deep oxidation reactions are minimized under these conditions. The mechanism of methanol formation is believed to involve the methylperoxy radical ($CH_3OO \cdot$) which abstracts hydrogen from methane. Unfortunately, up until now the per pass yields have been limited. This limited yield has been rationalized as resulting from the low reactivity of the C-H bonds in methane vis-a-vis the higher reactivity of the primary oxygenated product, methanol, which results in selective formation of the deep oxidation products CO and $CO_2$ when attempts are made to increase conversion.

U.S. Pat. No. 4,618,732 to Gesser et al. describes an improved homogeneous process for converting natural gas to methanol. The selectivity for methanol is ascribed by the inventors to careful premixing of methane and oxygen and to eliminating reactor wall effects by use of glass-lined reactors.

It is an object of this invention to selectively convert a gaseous feed comprising methane to higher-valued liquid oxygenates.

It is a further object to provide a selective method for the direct homogeneous partial oxidation of a gaseous hydrocarbon feed comprising methane to methanol.

It is a still further object of this invention to provide a method for converting a mixture of natural gas and oxygen to methanol and other high-valued oxygenates with increased selectivity and/or yield.

These and other objects will become evident to one skilled in the art on reading this entire specification and appended claims.

BRIEF DESCRIPTION OF THE DRAWING

FIG. 1. APPARATUS.

DESCRIPTION OF THE INVENTION INCLUDING BEST MODE

Surprisingly, we have now found that both the yield and the selectivity in the direct homogeneous partial oxidation of a gaseous feed comprising methane and gaseous oxygen are improved when the empty reactor is packed with a low surface area solid such as sand. Inasmuch as sand is not recognized as having an effect on organic chemical reactions, its effect in the present instance is not understood.

It is contemplated that any inert inorganic solid having a low surface area can be used in the present invention. The term "inert" as used herein means that the solid is unaffected physically or chemically by exposure to the feed at reaction temperature, and that it is devoid of patent catalytic activity for the direct partial oxidation of methane. Non-limiting examples of refractory solids contemplated as useful in the present invention include sand, crushed quartz, Vycor, and non-hydrous aluminas such as corundum (alpha alumina). In general, the surface area of the particulate solid is not more than 50 $M^2/g$ (square meters/gm), preferably not more than 10 $M^2/g$ and most preferably not more than 1 $M^2/g$, as determined by the B.E.T. method using nitrogen adsorption. Although it is contemplated that in some instances the packing material may be provided as a monolith, the more generally useful, less expensive preferred form is as a particulate solid.

In the practice of the present invention, it is preferred to use a dual flow system, i.e., a system in which the natural gas and the oxygen or air are kept separate until mixed just prior to being introduced into the reactor. However, if desired, the oxygen and natural gas may be premixed and stored together prior to the reaction. The preferred dual flow system minimizes the risk of fire or explosion. In the dual flow system, the amount of oxygen flow is controlled so as to prepare a reaction mixture that contains 2 to 20 percent by volume, more preferably 2 to 10 percent of oxygen. Air may be used instead of oxygen. The residence time of the gaseous feed in the reactor, computed in all cases herein on an empty reactor basis, is within the range of about 0.1 to 100 minutes, preferably about 2 to 10 minutes, and most preferably about 4 to 8 minutes.

The temperature in the reaction zone is from about 300° C. to 500° C., and preferably about 350° C. to 450° C. In the preferred mode of operation, the reactor temperature is at least sufficient to insure conversion of substantially all of the oxygen, i.e., more than 90% of the oxygen in the feed, and preferably more than 95%.

The apparatus shown in FIG. 1 of the drawing, which was used in generating the examples which follow, will now be described.

A methane source such as natural gas is fed via line 1 through valve 2 and passes via line 3 to a mass flow controller 4. It is then passed through check valve 5 and via line 6 passed to one arm of a mixing cross 7, another arm of which is fitted with a pressure gauge 14. The gaseous oxygen source is passed through line 8, through valve 9 and line 10 to mass flow controller 11, check valve 12 and then via line 13 to a third arm of the mixing cross 7. The mixed gasses exit the mixing cross 7 via the fourth arm, and pass through line 15 to mixing coil 16. The mixing coil consists of 40 feet of ⅛ inch O.D. tubing. The gas exits from the mixing coil and flows via line 7 which is fitted with a sand-filled filter 18, a T-fitting 19, a mass flow controller 20 and check valve 21. The gas mixture exiting from check valve 21 passes via line 22 to the inlet section of reactor 23 which is mounted in furnace 24. To maintain a constant pressure at the inlet to the reactor, one arm of the T-fitting 19 is connected to a Grove loader back pressure regulator 25 fitted with pressure gauge 26 and a bleed-off vent line 27. The pressure in line 22 and at the inlet to the reactor is indicated by pressure gauge 28. After passing through the Pyrex-lined reactor 23 mounted in furnace 24, hot gasses exiting the reactor pass via line 29 to a Grove loader back-pressure regulator 30 fitted with pressure gauge 31. The Grove loader is fitted with auxiliary line 32 and valves 34 and 35 connected to line 32 by a T-fitting. During start up of the run, valve 35 is closed and valve 34 is open, and the gasses exiting from the Grove loader are vented from valve 34 via line 33. After the temperature of the reactor has been adjusted, valve 34 is closed and the gasses passing from the Grove loader back-pressure regulator pass via line 37 to serially arranged cold trap 38, 39 and 40 via lines 41 and 42. The cold gas is then passed via line 43 to gas sample bomb 44, and then via line 45 to wet test meter 46 from whence they are vented via line 47.

EXAMPLES

The following examples are intended to illustrate the present invention without limiting the scope thereof, which scope is defined by this entire specification including appended claims. All amounts, proportions and selectivities shown are on a weight basis unless explicitly stated to be otherwise.

The following terms are defined. "Total Hydrocarbon Conversion" refers to the percentage of feed carbon converted when natural gas feedstock is used. "Selectivity" is defined as the percentage of carbon in a specific product, e.g. methanol, etc., formed from the converted feed carbon. "Yield" is defined as the product of conversion and selectivity. "Residence Time" in all cases refers to that calculated by dividing the volume of the empty reactor by the volume of feed at reaction temperature and pressure fed per minute to the reactor.

Experiments were run in the following manner. When reactor materials were used, 8.0 cc of 20/40 mesh gamma-alumina, (Na)ZSM-5, or 30/80 mesh washed sand were mixed with 8.0 cc of 30/80 mesh washed sand and loaded into a 16.5 mm i.d. Pyrex-lined reactor. The runs were performed using natural gas feed and the composition of the natural gas is given in Table I. (Na)ZSM-5 as used herein means sodium-exchanged ZSM-5.

TABLE I

| Composition of Natural Gas Feed | |
|---|---|
| Component | Vol. % |
| Methane | 95.66 |
| Ethane | 2.46 |
| Propane | 0.33 |
| Butanes | 0.12 |
| $C_5$'s | 0.01 |
| $CO_2$ | 0.90 |
| $H_2$ | 0.52 |
| | 100.00 |

6-7 volume percent of oxygen was co-fed and thoroughly premixed with the hydrocarbon feed prior to reaction in the apparatus shown in FIG. 1.

Operating conditions for the experiment were 360°-450° C. (minimum temperature required for complete $O_2$ consumption), 960 psig, and 400 cc/min feed flow (4 min. residence time based on empty tube). Gas products were determined by a Carle refinery gas analyzer and liquid products were analyzed by GC/MS. Liquid-phase oxygenates other than methanol were not quantified individually, but contained compounds such as formic acid, acetic acid, ethanol, dimethoxymethane, etc.

EXAMPLE 1 (Control)

This example is not within the scope of the present invention. It is included only for comparison.

In this example, the apparatus described in FIG. 1 with no packing in the pyrex-lined reactor was used to convert a feed mixture of natural gas and oxygen. The run conditions and results for all four examples are summarized in Table II to provide convenient comparison.

EXAMPLE 2

This example illustrates the invention using a washed, meshed sand packing instead of the empty reactor.

The results in Table II clearly demonstrate a marked improvement in both selectivity for methanol plus other liquid oxygenates and yield of methanol plus other oxygenates per pass.

EXAMPLE 3

This example is not within the scope of the present invention. In this example gamma alumina was substituted for the sand packing of Example 2.

EXAMPLE 4

This example, too, is not within the scope of the present invention and it is shown only for comparison. In this example (Na)ZSM-5 packing was substituted for the sand of Example 2.

TABLE II

| Example No. | 1 | 2 | 3 | 4 |
|---|---|---|---|---|
| Packing | None | Sand | γ-Alumina | (Na)ZSM-5 |
| Surface Area, $M^2/g$ | NA | <5 | 244 | 208 |
| Alpha Value | 0 | <1 | ca 1 | 1-2 |
| Pressure, psig | 960 | 960 | 960 | 960 |
| Temperature, °C.[1] | 360 | 400 | 450 | 410 |
| Residence Time, min. | 4 | 4 | 4 | 4 |
| Feed Flow, cc/min. | 400 | 400 | 400 | 400 |
| $O_2$ in Feed, % | 6.4 | 7.0 | 6.6 | 6.6 |
| $CH_4$ Conv., % | 3.6 | 4.0 | 3.1 | 2.4 |
| $C_2$ Conv., % | 28.4 | 27.2 | 23.0 | 25.1 |
| $C_3$ Conv., % | 59.0 | 49.6 | 55.9 | 44.4 |
| $C_4$ Conv., % | 79.7 | 64.2 | 76.5 | 57.6 |
| Total Hydrocarbon Carbon Conv., % | 5.5 | 5.9 | 5.1 | 4.3 |
| Product Selectivities | | | | |
| CO, % | 49.4 | 40.0 | 48.2 | 58.7 |
| $CO_2$, % | 21.8 | 21.7 | 24.0 | 20.8 |
| $CH_3OH$, % | 25.8 | 27.2 | 21.6 | 14.2 |
| Other Oxygenates, % | 3.0 | 11.1 | 6.3 | 6.4 |
| $CH_3OH$ + Other Oxygenates, % | 28.8 | 38.3 | 27.9 | 20.6 |
| % Yield, $CH_3OH$ + Other Oxygenates | 1.6 | 2.3 | 1.4 | 0.9 |

[1] Minimum temperature required for complete $O_2$ consumption.

What is claimed is:

1. A method for the direct oxidation of methane to methanol wherein a feed mixture consisting of a source of methane and gaseous oxygen, air, or a mixture thereof is passed through a reaction zone at an elevated pressure of about 10 to 100 atmospheres, an elevated temperature of about 300° to 500° C., and at a feed rate adjusted to provide a residence time of about 0.1 to 100 minutes, thereby forming an effluent comprising methanol, unreacted methane, and other oxygenates, said method comprising:

packing said reaction zone with an inorganic, particulate solid having a surface area of not more than 50 $M^2/g$ and passing said feed mixture through said packed reaction zone, said inorganic solid being selected from the group consisting of sand, quartz, Vycor and non-hydrous aluminas.

2. The method described in claim 1 wherein said inorganic solid has a surface area of not more than 10 $M^2/g$.

3. The method described in claim 1 including the step of maintaining said reaction zone at a temperature effective to form an effluent substantially free of gaseous oxygen.

4. The method described in claim 2 including the step of maintaining said reaction zone at a temperature effective to form an effluent substantially free of gaseous oxygen.

5. The method described in claim 1 wherein said inorganic solid is sand.

6. The method described in claim 3 wherein said inorganic solid is sand.

7. A method for the direct partial oxidation of methane to methanol, which method comprises:

intimately mixing a source of methane with a stream of gaseous oxygen, air, or a mixture thereof whereby forming a feed mixture containing about 1 to 20 volume percent gaseous oxygen; and, contacting under conversion conditions said feed mixture with a particulate bed of a refractory inorganic solid, said conversion conditions including a pressure of about 10 to 100 atmospheres, a temperature of about 300° to 500° C., and a contact time of about 1.0 to 100 minutes, whereby forming an effluent comprising methanol, other liquid oxygenates, and unreacted methane, wherein said refractory inorganic solid is chosen from the group consisting of sand, quartz, Vycor and a non-hydrous alumina.

8. The method described in claim 7 wherein said refractory inorganic solid is sand.

9. The method described in claim 8 wherein said temperature is above the minimum temperature effective to react substantially all of said gaseous oxygen in said feed mixture.

10. The method described in claim 9 wherein said temperature is about said minimum temperature.

11. The method described in claim 8 including the steps of recovering and recycling said unreacted methane.

* * * * *